US00PP10800P

United States Patent [19]

Wain

[11] Patent Number: Plant 10,800

[45] Date of Patent: Feb. 23, 1999

[54] CHRYSANTHEMUM PLANT NAMED 'JOSE SUNSET LADY'

[75] Inventor: Peter Wain, Hayling Island, United Kingdom

[73] Assignee: Cleangro, Ltd., West Sussex, England

[21] Appl. No.: 838,352

[22] Filed: Apr. 8, 1997

[51] Int. Cl.[6] ..... A01H 5/00

[52] U.S. Cl. ..... Plt./78

[58] Field of Search ..... Plt./76, 78

[56] References Cited

U.S. PATENT DOCUMENTS

| | | | |
|---|---|---|---|
| P.P. 5,995 | 5/1987 | Duffett et al. | Plt./78 |
| P.P. 6,403 | 11/1988 | Mack et al. | Plt./78 |
| P.P. 8,924 | 10/1994 | Hesse | Plt./78 |

*Primary Examiner*—Howard J. Locker

*Attorney, Agent, or Firm*—Christie, Parker & Hale, LLP

[57] ABSTRACT

A new plant variety of Chrysanthemum having medium yellow flowers with a maroon eye.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Jose Sunset Lady.'

'Jose Sunset Lady' was discovered as a naturally occurring mutation on a single branch in a controlled cultivated planting of the variety 'Sunset Lady', U.S. Plant Pat. No. 8,924. The new variety has been asexually reproduced by vegetative cuttings in Ventura County, Calif. and the distinguishing characteristics are retained through successive generations of asexual reproduction.

SUMMARY OF THE INVENTION

'Jose Sunset Lady' is a spray type pot forcing Chrysanthemum plant variety producing medium yellow flowers with a maroon eye and capable of being grown commercially in a greenhouse.

Comparison With Parent

In side-by-side comparisons of plants grown under the same conditions, the new variety achieves a height of about 29 cm compared to 25 cm for 'Sunset Lady'. The new variety also differs in flower coloration from the parent inasmuch as the new variety shows a much stronger red-maroon eye than does 'Sunset Lady'.

BRIEF DESCRIPTION OF ILLUSTRATIONS

The accompanying photographs show typical specimens of the new variety with colors being as nearly true as possible with illustrations of this type. One illustration shows, 'Jose Sunset Lady' grown as a pinched pot mum and the other illustration is a close-up of the flowers.

DESCRIPTION OF THE PLANT

The following description of the new variety is of specimens grown in a greenhouse in Ventura County, Calif. in the month of October. 'Jose Sunset Lady' has not been observed under all possible environmental conditions. The phenotype may vary significantly with variations in the environment such as temperature, light intensity, day length and cultural conditions. Color values are taken from The Royal Horticultural Society Colour Chart.

Plants of the new variety have been grown successfully under temperature conditions averaging about 65° F. at night and about 75°–85° F. during the day under light conditions of about 5,000–6,000 foot candles. The plants respond well to use of growth retardant, such as one treatment of B-9 at about 2000 ppm. To produce a commercial product the plants may be pinched once with the center bud removed. It has been observed that the shelf life of 'Jose Sunset Lady' is about 24 days with the response time of about 9 weeks.

Plant

Habit: Upright but loose and branching.

Height: About 29 cm after one application of the growth regulator as described.

Branching characteristics: Fair to good branching.

Number of breaks from pinch: About 3.

Typical container size to be grown in: 4", 6", 8", 10".

Length of lateral branches: Average—about 24 cm.

Stem color: Near 143C.

Foliage

Leaf arrangement: Alternate.

Number of leaves per lateral branch: Average—about 10, not very leafy, and leaves fall off easily.

(1) *Size.*—Length — Average about 6.7 cm. Width — Average about 3.9 cm.

(2) *Shape.*—Ovate.

(3) *Attachment.*—Petioled.

(4) *Apex.*—Obtuse.

(5) *Base.*—Tapered.

| (6) Color: | Mature | Young |
|---|---|---|
| Top: | Near 137A | Near 137B |
| Bottom: | Near 138A | Near 138B |

Margin: Lobed with very slight serrations.

Aspect: Slightly curled under.

Surface characteristics:

*Top.*—Puberulent.

*Bottom.*—Puberulent.

Venation: Palmately net; main veins prominent on underside of leaf; main vein coloration is near 137B, veinlet coloration is near 138A.

Petiole:

(1) *Length.*—About 1cm.

(2) *Color.*—Near 143C.

(3) *Other characteristics.*—Winged.

Stipule: About 2 per mature leaf, 3-lobed, sometimes 4-lobed, acute tips.

Flower

Inflorescence form: Cymose cluster.
Flower form: Decorative.
Flower shape: Irregular circle.
Flower color (general): Medium yellow with maroon eye.
Blooms: About 3–4 blooms per branch.
(1) *Diameter.*—About 6.5 cm.
(2) *Depth.*—About 2 cm.
(3) *Longevity on plant.*—About 24 days.
Sepal:
(1) *Number.*—About 30.
(2) *Color.*—Near 137A.
(3) *General appearance.*—Pubescent, membranous margin.
Peduncle:
(1) *Length.*—Average about 6.5 cm.
(2) *Habit.*—Curved.
(3) *Surface.*—Tomentose.
(4) *Color.*—Near 138B.
(5) *Strength.*—Average, very flexible.
Bud:
(1) *Shape.*—Very flat sphere.
(2) *Diameter.*—Avg. about 0.9 cm.
(3) *Color.*—Near 137D, shows petal color very early.
(4) *Height.*—About 0.4 cm.
Ray florets:
(1) *Number per flower.*—About 200.
(2) *Texture.*—Matte.
(3) *Shape.*—Elliptic, outermost ray florets are infrequently 2–3 lobed, lobes are about 0.8 cm in depth.
(4) *Apex.*—About 3 very small lobes.
(5) *Base.*—Tapered.
(6) *Margin.*—Entire.
(7) *Aspect.*—Mature reflex under, younger reflex up.
(8) *Length.*—Avg. About 3cm.
(9) *Width.*—Avg. About 1cm.
*Color—top side.*—Immature: Near 9B with streaks of near 59A. Mature: Near 8C. Fading: Near 6D.
*Color—under side.*—Immature: Near 47B with streaks of near 12B. Mature: Near 11C with streaks of near 47C. Fading: Near 11D with streaks of near 11A.
Disc florets:
(1) Number per flower: About 35, apex of disk florets is near 46A.
(2) Texture: Shiny.
(3) Shape: Cylindric.
(4) Margin: Entire.
(5) Length: About 0.3 cm.
(6) Width: About 0.09 cm.
(7) Fragrance: Not apparent.
*Color.*—Immature: Near 15C. Mature: Near 21B, green tip with maroon dot at apex. Fading: Near 22C.
Description of flower as it ages: Color loses vibrancy; flowers keeps shape and does not open to sphere; maroon coloration of center is maintained and ray florets in center have maroon tips, although outer ray florets do not maintain maroon tips.

Reproductive Organs

Ray Florets:
*Pistillate.*—(1) Pistil number: 1 per floret. (2) Ovary shape: Half sphere. (3) Stigma shape: Forked, angled out slightly. (4) Stigma color: Near 12A. (5) Style length: About 0.5 cm. (6) Style color: Near 154A.
Disc florets: Both staminate and pistillate.
*Pistillate.*—(1) Pistil number: 1 per floret. (2) Stigma shape: linear, flared out slightly, near 1B. (3) Style length: About 0.2 cm, clear in color.
*Staminate.*—(1) Stamen number: About 6. (2) Anther length: About 0.11 cm. (3) Anther shape: linear, very narrow. (4) Pollen color: Near 17A. (5) Pollen quantity: Quantity varies among individual disk florets from moderate to abundant.

What is claimed is:

1. A new and distinct variety of Chrysanthemum plant substantially as herein shown and described.

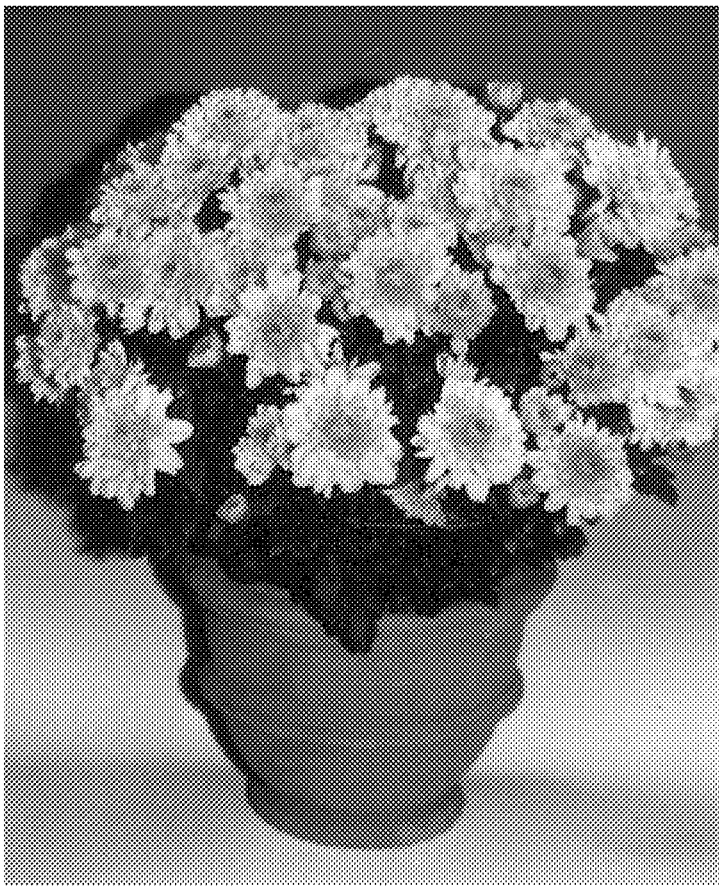

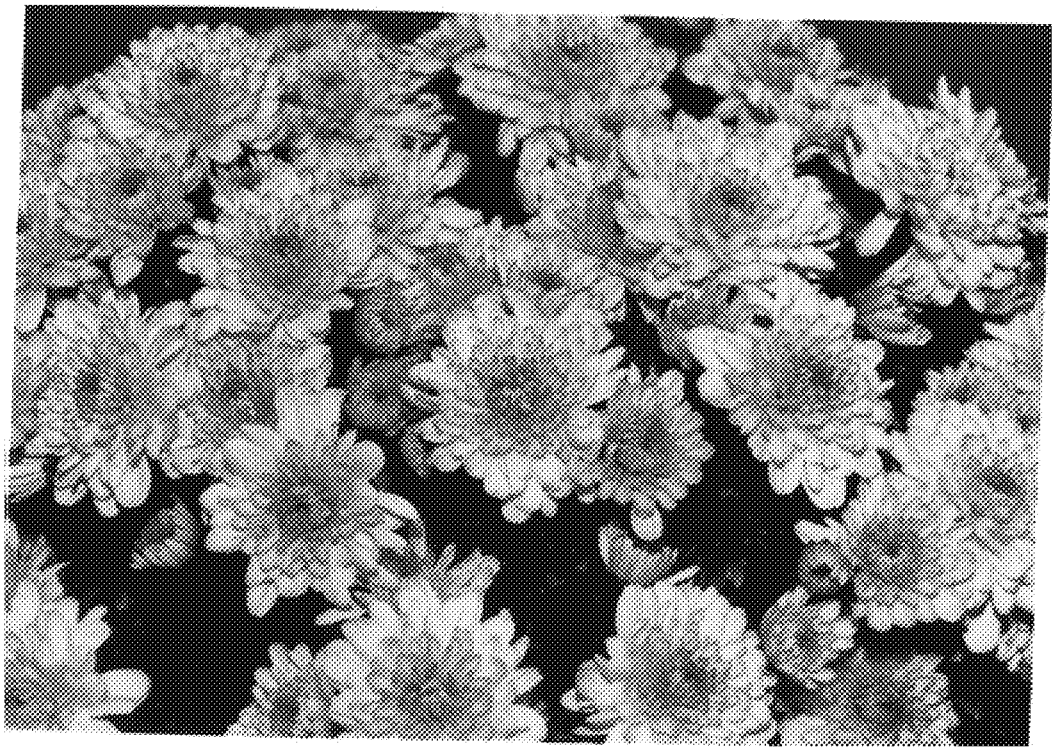

* * * * *